(12) United States Patent
Corver et al.

(10) Patent No.: US 7,015,693 B2
(45) Date of Patent: Mar. 21, 2006

(54) NMR MEASURING SYSTEM FOR WEIGHT AND HUMIDITY OF POWDERS

(75) Inventors: Jozef A. W. M. Corver, Nuenen (NL); Paul Stewart, Youngstown, NY (US)

(73) Assignee: The BOC Group, Inc., Murray Hill, NJ (US)

( * ) Notice: Subject to any disclaimer, the term of this patent is extended or adjusted under 35 U.S.C. 154(b) by 0 days.

(21) Appl. No.: 10/836,738

(22) Filed: Apr. 30, 2004

(65) Prior Publication Data

US 2005/0122104 A1    Jun. 9, 2005

Related U.S. Application Data

(60) Provisional application No. 60/471,232, filed on May 16, 2003.

(51) Int. Cl.
G01V 3/00    (2006.01)
(52) U.S. Cl. .................................. 324/300; 324/307
(58) Field of Classification Search ................ 324/300, 324/307, 309, 312, 314, 318, 322
See application file for complete search history.

(56) References Cited

U.S. PATENT DOCUMENTS

| | | |
|---|---|---|
| 3,798,873 A | 3/1974 | Ledgett |
| 4,727,325 A | 2/1988 | Matsui et al. |
| 5,015,954 A | 5/1991 | Dechene et al. |
| 5,049,819 A | 9/1991 | Dechene et al. |
| 5,291,422 A | 3/1994 | Esztergar |
| 5,302,894 A | 4/1994 | Dechene et al. |
| 5,302,896 A | 4/1994 | Dechene et al. |
| 6,028,428 A | 2/2000 | Cunningham et al. |
| 6,362,619 B1 | 3/2002 | Prammer et al. |
| 6,377,049 B1 | 4/2002 | Benz et al. |
| 6,426,058 B1 | 7/2002 | Pines et al. |
| 6,759,601 B1 * | 7/2004 | Petty et al. .................... 177/1 |

FOREIGN PATENT DOCUMENTS

| | | |
|---|---|---|
| DE | 1803372 A1 | 5/1970 |
| GB | 2149509 A | 6/1985 |
| WO | WO 99/67606 A1 | 12/1999 |

OTHER PUBLICATIONS

Derwent WPI Abstract, UNILEVER NV, Package Weight Measuring System, NL 154001B, Jul. 15, 1977, (Corresponds to DE 1803372A1).

* cited by examiner

*Primary Examiner*—Louis Arana
(74) *Attorney, Agent, or Firm*—Bernard Lau

(57) ABSTRACT

An improvement in a magnetic resonance method for determining the mass of samples wherein the samples include powdered solid materials, including applying a first magnetic field in a first direction in an interrogation zone for creating a net magnetisation within a sample located within the interrogation zone; applying an alternating magnetic field in a second direction in the interrogation zone for temporarily changing the net magnetisation of the sample; monitoring energy emitted by the sample as the net magnetisation of the sample returns to its original state and generating an output signal having a characteristic which is proportional to the energy emitted; comparing the output signal characteristic with like data obtained from at least one similar sample of known mass; and, determining the mass of the sample; the improvement being one of generating the static magnetic field having a field strength in the range of about 0.1 T to about 1.3 T, or disposing the samples within a distance of about 0.5 mm from the surface of the magnetic probe generating the static magnetic field; applying the alternating magnetic field to the sample; sensing the free induction decay energy of the sample and generating a corresponding output free induction decay signal.

13 Claims, 12 Drawing Sheets

FIG. 4

NMR MEASURING SYSTEM FOR WEIGHT AND HUMIDITY OF POWDERS

CROSS REFERENCE TO RELATED APPLICATIONS

This application claims the benefit of the filing date of U.S. Provisional Application Ser. No. 60/471,232, filed May 16, 2003, which is incorporated herein by reference.

FIELD OF THE INVENTION

The invention relates to non-contact check weighing of samples using NMR techniques.

BACKGROUND

The nuclei of atoms that have a magnetic moment will have sharply defined frequencies of nuclear oscillation in a strong magnetic field (Larmor frequency). The frequency of oscillation of each atomic nucleus will depend on its mass, its dipole moment, the chemical bonding of the atom, the atom's environment (which will be affected by electromagnetic coupling to other atoms in the vicinity), and the strength of the magnetic field seen by the atom. Thus, the frequency of oscillation will be characteristic, not only of the various atomic species, but also of their molecular environments. By resonantly exciting these oscillations, the atomic species and their environments can be determined with accuracy. This phenomenon is known as "nuclear magnetic resonance," or NMR.

If a pulse of RF energy is applied at a resonance frequency of atoms of a particular species and environment (e.g. hydrogen atoms in a water environment), the atomic nuclei of this type and environment will resonantly be excited, and will later make a transition back to a low state of excitation. This transition is accompanied by emission of a radio-frequency signal, at the excitation frequency or a known lower frequency. The signal is known as the Free Induction Decay (FID) The amplitude and the shape of this FID-curve is related to the amount of nuclei involved in the process and to specific conditions and properties of the atoms in relation to the environment.

The use of NMR techniques in measurement, detection and imaging has become desirable in many scientific fields of endeavor. The non-invasive, non-destructive nature of NMR has facilitated application to industrial instrumentation, analysis and control tasks.

Almost every element in the periodic table has an isotope with a non-zero nuclear spin. This spin causes the nuclei to be magnetically active. Among magnetically active nuclei, NMR can only be performed on isotopes whose natural abundance is high enough to be detected. Commonly encountered magnetically active nuclei are $^1$H, $^{13}$C, $^{19}$F, $^{23}$Na, and $^{31}$P. The most common is $^1$H, which also possesses the largest magnetic moment, rendering it most advantageous for the performance of NMR spectroscopy.

Upon application to a sample of a static magnetic field, $B_o$, sample nuclear spins align with the field, parallel to the direction of the field. The magnetic moments can align themselves either parallel (NSNS) or antiparallel (NNSS) to the static field. Alignment parallel to the static field is the lower energy state and alignment against the field is the higher energy state. At room temperature, the number of nuclei having spins in the lower energy level, $N^+$, slightly outnumbers the number in the upper level, $N^-$. Boltzmann statistics provides that $$N^-/N^+ = \exp(-E/kT), \quad (1)$$

where E is the energy difference between the spin states; k is Boltzmann's constant, $1.3805 \times 10^{-23}$ J/Kelvin; and T is the temperature in Kelvin. As the temperature decreases, so does the ratio $N^-/N^+$. As the temperature increases, the ratio approaches unity.

Owing to the slight imbalance of nuclei having spins at the higher state, a sample in a static magnetic field will exhibit a magnetization parallel to the static field. Magnetization results from nuclear precession (relaxation) around the static magnetic field. The frequency of this precession depends on the strength of the static magnetic field, and is defined as:

$$v = \gamma B, \quad (2)$$

where B is the magnetic field strength and Gamma is the gyromagnetic ratio of at least one atom, typically hydrogen, in the sample material. The gyromagnetic ratio is related to the magnetic moment of the nucleus under analysis. The gyromagnetic ratio of protons is 42.57 MHz/Tesla. The frequency thus measured is known as the Larmor frequency, v, which can be conceptualized as the rate of precession of the nucleus in the static magnetic field or the frequency corresponding to the energy at which a transition between the upper and lower states can take place.

The fundamental NMR signal is derived by inducing transitions between these different alignments. Such transitions can be induced by exposing a sample to the magnetic component of an RF (radio frequency) signal, typically generated by an RF coil. When the magnetic component is applied perpendicularly to the magnetic field a resonance occurs at a particular RF frequency (identical to the precession frequency, the Larmor frequency), corresponding to the energy emitted or absorbed during a transition between the different alignments. When a strong magnetic field, such as in the range of 0.1–2 Tesla (1 T=10,000 Gauss) is used, this resonance typically occurs in the megahertz frequency range, corresponding to FM radio. Hence the radiation is known as Radio Frequency (RF) radiation.

The signal in NMR spectroscopy results from the difference between the energy absorbed by the spins which make a transition from the lower energy state to the higher energy state, and the energy emitted by the spins which simultaneously make a transition from the higher energy state to the lower energy state. The signal is thus proportional to the population difference between the states. NMR spectroscopy gains its high level of sensitivity since it is capable of detecting these very small population differences. It is the resonance, or exchange of energy at a specific frequency between the spins and the spectrometer, which gives NMR its sensitivity.

Pulsed NMR spectroscopy is a technique involving a magnetic burst or pulse, which is designed to excite the nuclei of a particular nuclear species of a sample being measured after the protons of such sample have first been brought into phase in an essentially static magnetic field; in other words the precession is modified by the pulse. Typically, the direction of the static magnetic field, $B_o$, is thought of as being along the Z-axis in three-dimensional space. At equilibrium, the net magnetization vector lies along the direction of the applied magnetic field $B_o$ and is called the equilibrium magnetization $M_o$. In this configuration, the Z component of magnetization $M_Z$ equals $M_o$. $M_Z$ is referred to as the longitudinal magnetization. There is no transverse ($M_X$ or $M_Y$) magnetization in such a case.

It is possible to change the net magnetization by exposing the nuclear spin system to energy of a frequency equal to the energy difference between the spin states. If enough energy is put into the system, it is possible to saturate the spin system and make $M_Z=0$. The time constant, which describes how $M_Z$ returns to its equilibrium value, is called the spin lattice relaxation time ($T_1$). The equation governing this behavior as a function of the time t after its displacement is:

$$M_Z = M_0 (1 - e^{-t/T_1}) \quad (3)$$

$T_1$ is therefore defined as the time required to change the Z component of magnetization by a factor of e. Hence, at $t=T_1$, $M_Z=0.63\ M_0$. In order to properly perform repeated measurements, which is necessary in order to reduce background noise and enhance signal quality, $M_0$ should be allowed to return to $M_Z$. In other words, the longitudinal magnetization $M_Z$, which equals zero upon saturation, should be allowed to fully return to the +Z direction and attain its equilibrium value of $M_0$. While this theoretically would take forever, (i.e., following saturation, $M_Z=M_0$ when $t=\infty$), it is generally considered sufficient when $M_Z=0.99\ M_0$, which occurs when $t=5T_1$. This places time constraints on the speed at which a sample may be measured multiple times or the overall throughput of samples through an interrogation zone.

If the spin system is oversaturated, forcing the net magnetization into the −Z direction, it will gradually return to its equilibrium position along the +Z axis at a rate also governed by $T_1$. The equation governing this behavior as a function of the time t after its displacement is:

$$M_z = M_0 (1 - 2e^{-t/T_1}) \quad (4)$$

The spin-lattice relaxation time ($T_1$) is the time to reduce the difference between the longitudinal magnetization ($M_Z$) and its equilibrium value by a factor of e. Here, too, an elapsed time of $t=5\ T_1$ is required in order for $M_Z$ to return to a value of 0.99 $M_O$, placing a similar time constraint on sample throughput.

If the net magnetization is rotated into the XY plane by a 90° pulse, it will rotate about the Z-axis at a frequency equal to the frequency of a photon, having the energy corresponding to a transition between the two energy levels of the spin. This frequency is called the Larmor frequency. In addition to the rotation, the net magnetization, now in the XY plane, starts to dephase because each of the spin packets making it up is experiencing a slightly different magnetic field and hence rotates at its own Larmor frequency. The longer the elapsed time, following the pulse, the greater the phase difference. If the detector coil is sensitive to measurements of fields in the X-direction alone, the dephasing results in a decaying signal, eventually approaching zero. The time constant, which describes this decay of the transverse magnetization, $M_{XY}$, is called the spin-spin relaxation time, $T_2$.

$$M_{XY} = M_{XY0} e^{-t/T_2} \quad (5)$$

$T_2$ is always less than or equal to $T_1$. The net magnetization in the XY plane goes to zero and then the longitudinal magnetization grows until $M_o$ returns to the +Z direction. Any transverse magnetization behaves the same way.

The spin-spin relaxation time, $T_2$, is the time to reduce the transverse magnetization by a factor of e. The difference between spin-lattice relaxation and spin-spin relaxation is that the former works to return $M_z$ to $M_0$, while the latter works to return $M_{xy}$ to zero. $T_1$ and $T_2$ were discussed separately above, for clarity. That is, the magnetization vectors are considered to fill the XY plane completely before growing back up along the Z-axis. Actually, both processes occur simultaneously, with the only restriction being that $T_2$ is less than or equal to $T_1$.

Two factors contribute to the decay of transverse magnetization—(1) molecular interactions (said to lead to a pure $T_2$ molecular effect), and (2) variations in $B_o$ (the applied static field), said to lead to an inhomogeneous $T_2$ effect. The combination of these two factors is what actually results in the decay of transverse magnetization. The combined time constant is called "$T_2$ star" and is given the symbol $T_2^*$. The relationship between the $T_2$ from molecular processes and that from inhomogeneities in the magnetic field is $$1/T_2^* = 1/T_2 + 1/T_{2inh}. \quad (6)$$

The source of the inhomogeneities can be natural fluctuations in a field, or imperfections in the magnets generating the field or magnetic contaminants, such as iron or other ferromagnetic metals.

In practice, to actually measure a sample using NMR, a sample is first placed in a static magnetic field, $B_o$, which is the interrogation zone of the instrument. Next, a magnetic pulse is applied, which rotates the magnetization vector to a desired extent, typically 90° or 180°. A 90° pulse, for example, rotates the magnetization vector from the Z-direction into the XY plane resulting in transverse magnetization, $M_{XY}$, as discussed above. After the application of the pulse, there occurs a free induction decay (FID) of the magnetization associated with the excited nuclei.

Traditional Fourier Transform analysis transforms a time domain spectrum (amplitude of magnetization vectors vs. time) into a frequency domain spectrum (frequency vs. relative amplitude), which separates individual frequencies out of a multiphase spectrum. This separation can be used to advantage in studying the nuclei of interest. The duration of the pulses, the time between the pulses, the pulse phase angle and the composition of the sample are parameters, which affect the sensitivity of this technique.

International Patent Application No. WO9967606, incorporated herein by reference as if fully written out below, describes a check weighing system for samples on a production line, including a magnet for creating a static magnetic field over an interrogation zone to create a net magnetization within a sample located within the interrogation zone, and an RF coil for applying an alternating magnetic field over the interrogation zone to cause excitation of the sample according to the principles of NMR.

The use of NMR for techniques for check weighing samples on a production line encounters a variety of difficulties, including but not limited to the presence of interfering species such as metal particles either within the sample container or elsewhere in the system, effects of temperature on the magnet or electronics, humidity in the sample or system, and mechanical instability of the containers.

It would be desirable to provide a system and method for identifying and/or compensating for the above noted potential sources of imprecise measurements for an NMR sample check weighing system.

SUMMARY

The present methods relate to check weighing material contained in a container, which is passing along a product filling line, i.e. a production line, by nuclear magnetic resonance (NMR) techniques.

Currently there does not exist a measurement method to continuously measure the weight powders in a non-contact and non-destructive way (with 100% protocolling). Methods are provided to continuously measure powders by applying NMR techniques with 100% protocolling, and optionally to simultaneously measure moisture content, or humidity, of the powders.

An improvement is provided in a magnetic resonance method for determining the mass of samples in a production line wherein the samples comprise powdered solid materials, comprising: applying a first magnetic field in a first direction in an interrogation zone for creating a net magnetisation within a sample located within the interrogation zone; applying an alternating magnetic field in a second direction in the interrogation zone for temporarily changing the net magnetisation of the sample located within the interrogation zone; monitoring energy emitted by the sample as the net magnetisation of the sample returns to its original state and generating an output signal having a characteristic which is proportional to the energy emitted; comparing the output signal characteristic with like data obtained from at least one similar sample of known mass; and, determining the mass of the sample; characterised by: applying the first magnetic field having a field strength in the range of about 0.1 T to about 1.3 T; applying the alternating magnetic field to the sample; monitoring the free induction decay energy of the sample and generating an output free induction decay signal corresponding thereto.

An improvement is provided in a magnetic resonance method for determining the mass of samples in a production line wherein the samples comprise powdered solid materials, comprising: applying a first magnetic field in a first direction in an interrogation zone for creating a net magnetisation within a sample located within the interrogation zone; applying an alternating magnetic field with a probe in a second direction in the interrogation zone for temporarily changing the net magnetisation of the sample located within the interrogation zone; monitoring energy emitted by the sample as the net magnetisation of the sample returns to its original state and generating an output signal having a characteristic which is proportional to the energy emitted; comparing the output signal characteristic with like data obtained from at least one similar sample of known mass; and, determining the mass of the sample; characterised by: disposing the samples within a distance of about 0.1 to about 10 mm from the surface of the probe; applying the alternating magnetic field to the sample; and monitoring the free induction decay energy of the sample and generating an output free induction decay signal corresponding thereto.

BRIEF DESCRIPTION OF THE DRAWINGS

FIG. 4 is a chart of the statistics used to determine the time constant of FIG. 3.

DETAILED DESCRIPTION

Figure 1:
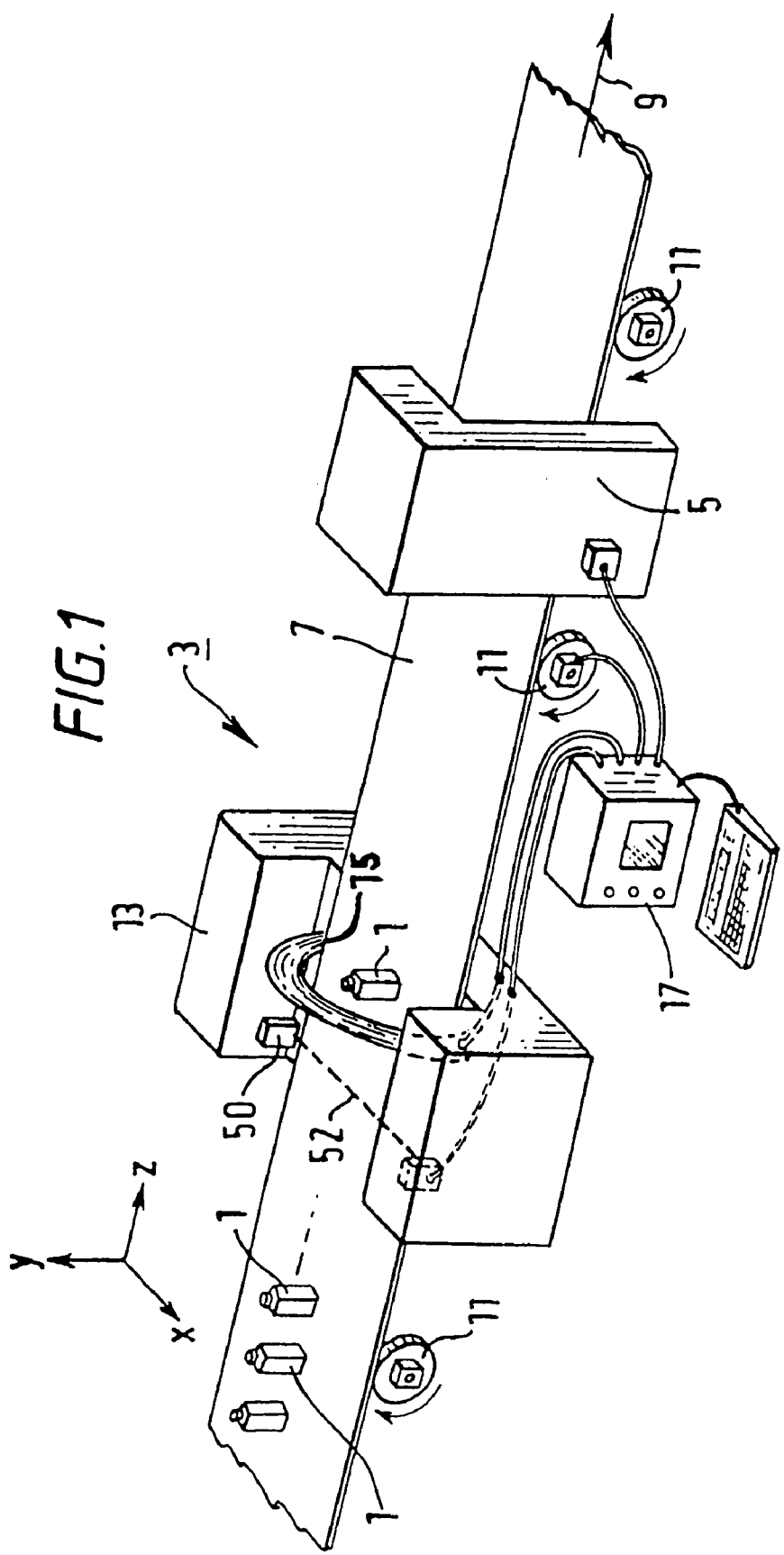
FIG. 1 is a schematic view of a production line with an NMR check weighing station for checking that each container passing through the weighing station has the desired amount of product.

The present methods relate to check weighing material contained in a container, which is passing along a production line, by nuclear magnetic resonance (NMR) techniques. As one example, check weighing is used by the pharmaceuticals industry for the monitoring and regulation of the amount of a drug in a sealed glass vial during filling. The drug weight can be as small as a fraction of a gram, and is required to be weighed with an accuracy of a few per cent or better, in a vial weighing tens of grams at a rate of several weighings per second. Conventionally, to obtain the required accuracy, it is necessary to remove the vials from the production line and to weigh them on precision balances both before and after filling in order to take into account the weight of the container. Because this is time-intensive, only a fraction of the product can be tested. If deviations from expected values are detected, a large batch of product can be wasted before the problem is identified. As the vial must be weighed both before and after filling, the weighing must be performed in an aseptic environment between filling and sealing.

An NMR apparatus for determining the mass of a sample generally may comprise means for generating a static magnetic field in a first direction through the sample; means for applying an alternating excitation magnetic field in a second different direction through the sample; means for sensing energy emitted by the sample in response to the excitation magnetic field and for outputting a signal in dependence thereon; and means for comparing the signal output by said sensing means with stored calibration data to provide an indication of the mass of the sample. Such an apparatus can be used on-line in a product filling line. It can provide a non-contacting measure of the mass of the contents of a container independently of the container mass, if the container is made of a material which is not responsive to NMR, and is useful for determining the mass of small quantities of sample such as samples weighing between 0.1 grams and 10 grams which may be contained in glass containers of 20 grams or more, providing an indication of mass and not weight of the sample.

The apparatus can be used to measure the contents of a container by filling the container with the predetermined amount of sample; transporting each of the filled containers to a weighing station; weighing the sample within each of the containers; sealing the sample within the container; and rejecting any containers which do not contain the predetermined amount of sample within a predetermined tolerance. The weighing of the sample includes generating a static magnetic field in a first direction through an interrogation zone for creating a net magnetization within a sample located within the interrogation zone; applying a pulse of alternating magnetic field in a second different direction through the interrogation zone for temporarily changing the net magnetization of the sample located within the interrogation zone; sensing energy emitted by the sample as the net magnetization of the sample returns to its original state and outputting a signal in dependence thereon; and comparing the signal output by the sensing step with calibration data which relates the mass of at least one similar sample of known mass to the corresponding signal output by the sensing step, to provide the indication of the mass of the sample within each container.

In addition to pharmaceuticals, such an apparatus and method can be used in a variety of applications, including but not limited to cosmetics, perfumes, industrial chemicals, biological samples and food products. It can measure high value products where 100% sampling can reduce wastage, and can be used to determine the mass of samples that are in solid form, in powder form, in liquid form and in gas form, or any combination thereof.

FIG. 1 shows a portion of a production line, which fills glass vials 1 with a drug sample. Included is a weighing station 3 that is provided "in-line" for weighing each of the filled vials that pass therethrough, and a reject station 5 that removes those vials from the line that do not have the sufficient amount of the drug to meet product specifications. The vials 1 are transported to the weighing station 3 from a filling (and optionally sealing) station (not shown) by a conveyor belt 7 which, as represented by the arrow 9, moves in the z direction through the action of rotating conveyor wheels 11. The weighing station uses NMR techniques to determine the mass of the drug sample within each of the glass vials 1. As those skilled in the art will appreciate, glass vials are useful as the container, because they do not give a signal that might interfere with the measurement process. In this embodiment, the weighing station 3 comprises a permanent magnet 13, an RF coil 15 and a computer control system 17. The magnet 13 is creates a homogeneous direct current (DC) or static magnetic field in the x direction across the conveyor belt 7. The sample in the glass vial contains nuclei which each possess a magnetic moment, e.g. 1H nuclei (protons). This magnetic moment, discussed above, is a result of the spin of the nuclei.

In most NMR systems, the static magnetic field strength is such that the Larmor frequency of the sample is in the radio frequency range of the electromagnetic spectrum. Applying an alternating current (AC) magnetic field to the sample at the sample's Larmor frequency and orientated orthogonal to the static magnetic field, will cause the sample's net magnetization to rotate about the AC magnetic field's axis, away from the direction of the static field. In this embodiment, this magnetic field is generated by applying a corresponding AC current to the RF coil 15. The angle of rotation of the net magnetization can be varied by varying the amount of energy delivered to the RF coil 15.

In this exemplified embodiment, an excitation field that causes a 90° rotation is used to excite the sample. After the 90° pulse has been applied to the sample, the sample is left in a high-energy, non-equilibrium state, from which it will relax back to its equilibrium state. As it relaxes, electromagnetic energy at the Larmor frequency is emitted, the magnetic component of which induces current in the RF coil 15, the peak amplitude of which varies with, among other things, the number of magnetic moments in the sample and hence the number of molecules in the sample. The received signal is then passed to the computer control system 17, which compares the peak amplitude of the signal received from the unknown sample, with the peak amplitude of a signal received from a calibration sample with a known mass (or weight), to determine the mass (or weight) of the sample being tested. The check weighing station 3 may be able to generate and receive signals at different Larmor frequencies needed to be able to excite different NMR responsive elements in samples. If the computer control system 17 can store calibration data for each of the different samples, then the check weighing station would be able to determine the mass of various samples using the NMR signals from the different NMR responsive elements.

As described in the exemplified embodiment, the RF probe monitors the energy emitted by the sample as the net magnetisation of the sample returns to its original state of equilibrium, and generates an output signal having a characteristic that is proportional to the energy emitted, such as current amplitude. The computer control system receives the RF probe output signal. A processor compares the current amplitude or other output signal characteristic with like data obtained from at least one similar sample of known mass, and determines the mass of the sample from the results of the comparison. It is to be understood that although for purposes of illustration the embodiment has been described as measuring the peak amplitude of the induced signal, any chemometric characterization technique can be used that derives a single value from the energy emitted and the output signal generated. In general, comparison techniques may include comparing the FID characteristics of the sample with like FID characteristics of at least one known sample, i.e., the calibration data.

The operation of one embodiment is described in detail with reference to FIG. 1f, a block diagram of the principal components of the computer control system 17 of this embodiment. The control system comprises a connection terminal 21 for connecting the control system to the RF coil 15. The connection terminal 21 is connectable, through switch 23, to a signal generator 25 and a power amplifier 27 which are operable to generate and amplify respectively the excitation signal which is applied to the RF coil 15. The connection terminal 21 is also connectable, through switch 23, to a receiving amplifier 31 which amplifies the signal received from the sample under test. This amplified signal is then filtered by the filter 33 to remove noise components and then passed to the mixer 35 where the received signal is down converted to an intermediate frequency (IF) by multiplying it with an appropriate mixing signal generated by the signal generator 25. The IF signal output by the mixer 35 is then filtered by the filter 37 to remove the unwanted components generated by the mixer 35. The filtered IF signal is then converted into a corresponding digital signal by the A/D converter 39 and is then passed to the microprocessor 41.

As shown by the dashed control lines 43 and 45, the microprocessor 41 controls the operation of the signal generator 25 and the switch 23. The microprocessor 41 may operate to ensure that the signal generator 25 generates the excitation signal when the filled vial 1 is at the desired location within the check weighing station 3. The microprocessor 41 knows when the vial 1 is at the correct location from a signal received from the position sensor electronics 47 which is connected, through connection terminal 49, to an optical position sensor 50 mounted in the check weighing station 3. Referring to FIG. 1, when the glass vial 1 passes by the optical position sensor 50, a light beam 52 is broken. This is detected by the position sensor electronics 47 which in turn signals the microprocessor 41. Based on this information and the speed of the conveyor belt 7 (provided by the conveyor controller 51), the microprocessor determines the appropriate timing for the application of the burst of excitation current and signals the signal generator 25 accordingly. Alternatively, using a timing belt, or any other system that continuously monitors position, the appropriate timing for the application of the burst of excitation current can be achieved.

As those skilled in the art of magnetic resonance will appreciate, it takes a finite period of time after the sample enters the static field generated by the magnet 13 for the net magnetisation of the sample to develop along the X-direction. If the excitation signal is applied to the RF coil 15 before the magnetisation has fully developed, then the strength of the signal generated by the sample will not be at its maximum.

The net magnetisation and thus the strength of the resultant signal produced by a sample varies with time in the static magnetic field. The longitudinal relaxation time depends upon the sample being tested. Therefore, given the type of sample which is being tested, the relaxation time can be determined. This information, combined with the speed of the conveyor belt 7, determines the minimum length of the magnet 13 in the Z-direction which is required to ensure that as large a signal as possible is generated by the sample under test. Given the limited amount of time and possibly the maximum allowable length of the magnet it is important to ensure identical treatment of consecutive samples in terms of position and speed.

In one embodiment, a capacitor (not shown) is connected across the ends of the RF coil 15 so that it is tuned to the Larmor frequency of the sample. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The Larmor frequency of an MR responsive element such as hydrogen is calculated by multiplying the static magnet's DC magnetic field strength by the gyromagnetic ratio for the element (which for hydrogen is 42.57 MHz/Tesla). The gyromagnetic ratio for other MR responsive elements can be found in CRC Handbook of Chemistry & Physics, published by CRC Press Inc. The tuning of the RF coil 15 in this way makes the system less susceptible to electromagnetic interference or to other MR signals from nuclei with different gyromagnetic ratios. The excitation current flowing through the RF coil 15 generates a corresponding magnetic field in the Z-direction. This excitation magnetic field causes the net magnetisation of the sample in the vial 1 to rotate or precess about the X-axis at the Larmor frequency. When the excitation current is removed from the RF coil 15, the nuclei in the sample begin to relax back to their equilibrium positions, emitting RF energy at the Larmor frequency as they do so. This induces a signal in the RF coil 15 which is seen to decay and its characteristic decay time is referred to as the transverse relaxation time. This depends upon the sample being tested and not on the static field strength.

As shown, the peak amplitude of the induced signal is at its maximum shortly after the excitation current stops, after which point the signal exponentially decays to zero. The peak amplitude of the signal induced in the RF coil 15 by the sample is directly proportional to the number of magnetic moments in the sample. Consequently, in this embodiment, the microprocessor 41 monitors the peak signal level which it receives from the A/D converter 39 after the excitation signal has been removed from the RF coil 15. Alternatively the microprocessor can determine the average signal over a period of time or fit the shape of the curve in order to improve accuracy.

In one embodiment, the microprocessor 41 then compares this peak signal level with calibration data obtained by testing a similar sample or samples of known mass, to provide an indication of the mass of the sample currently being tested. In this embodiment, this calibration data is obtained from a number of similar samples of different known masses during a calibration routine before the production batch is begun and is stored in memory 53. In this embodiment, the calibration data is a function which relates the peak amplitude of the MR signal received from the sample under test to the mass of the sample.

In one embodiment, if the microprocessor 41 determines that the mass of the current sample being analysed is not of the required mass within a given tolerance, it outputs a control signal on control line 55 to the reject controller 57. The reject controller then outputs a signal to output terminal 59 which is connected to the reject station 5, for causing the reject station to remove the current vial 1 being tested from the conveyor belt 7 when it arrives at the reject station 5.

Figure 1A:
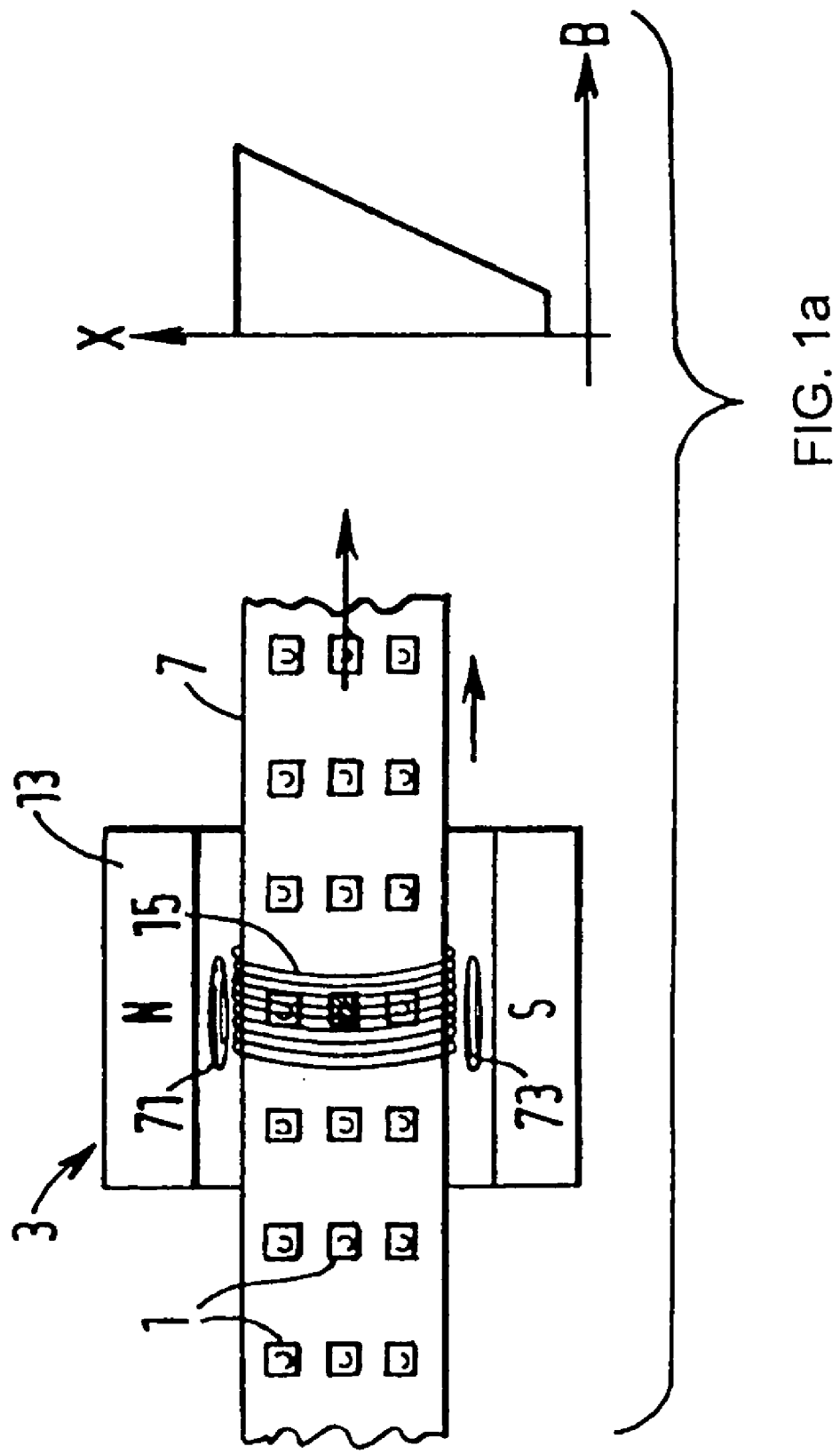
FIG. 1a diagrammatically illustrates the form of a check weighing station according to an alternative embodiment in which a magnetic field gradient is applied over an interrogation zone.
Figure 1B:
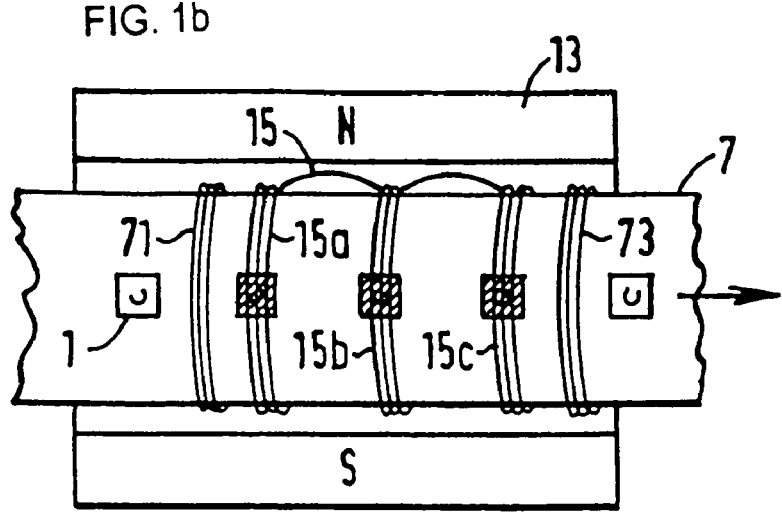
FIG. 1b diagrammatically illustrates an alternative check weighing station.
Figure 1C:
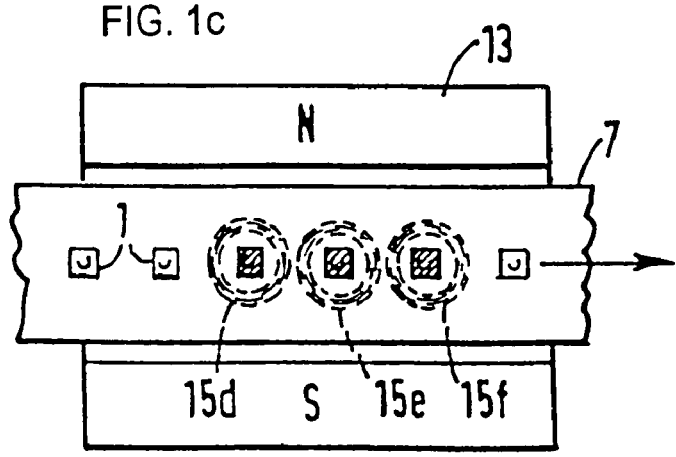
FIG. 1c illustrates a further check weighing station.
Figure 1D:
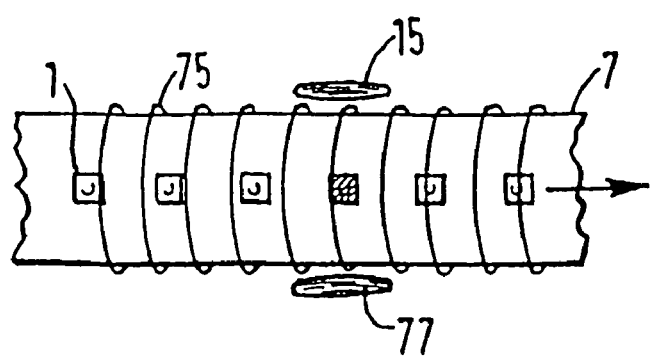
FIG. 1d illustrates another check weighing station.
Figure 1E:
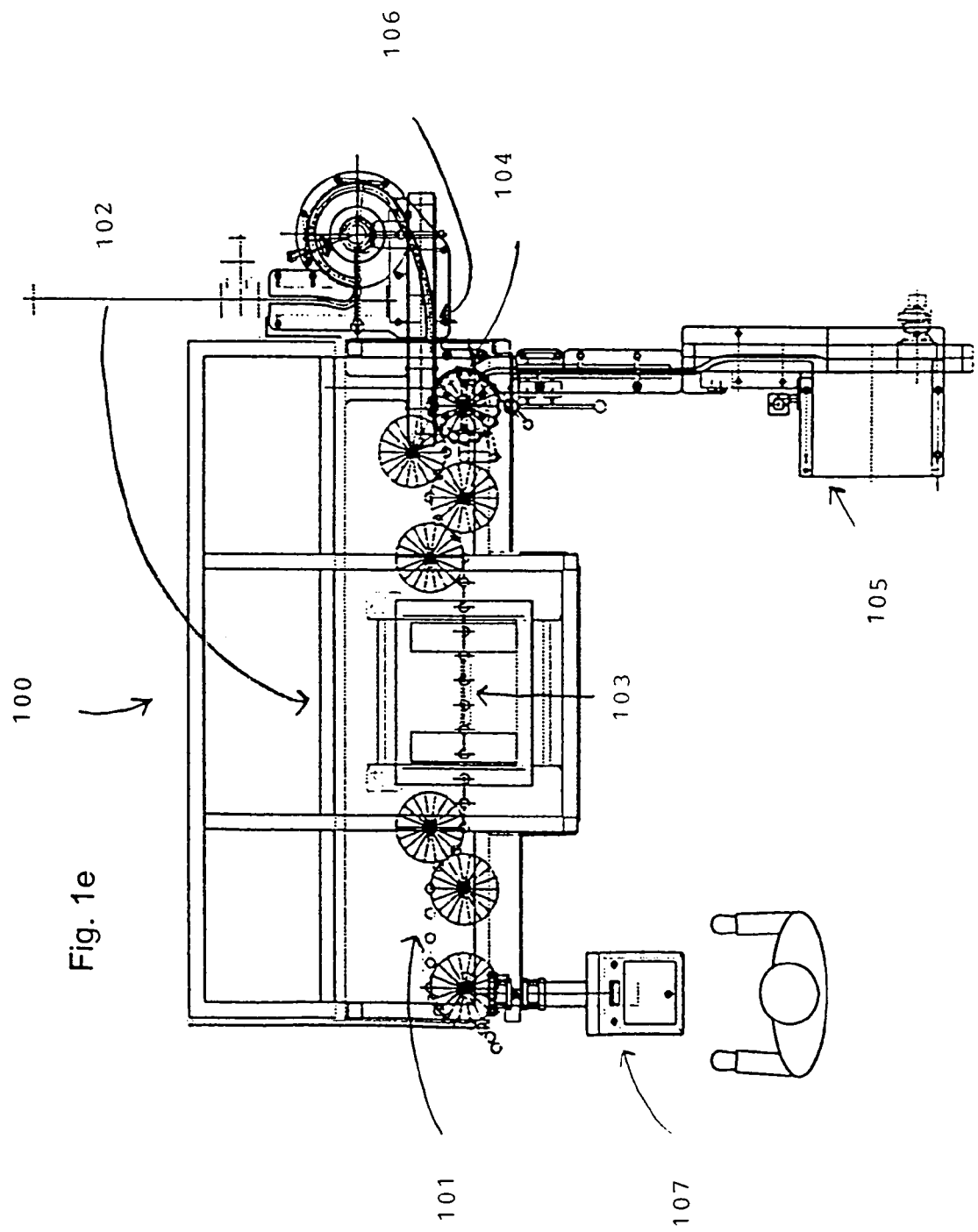
FIG. 1e is a schematic plan view of a production line with an NMR check weighing station
Figure 1F:
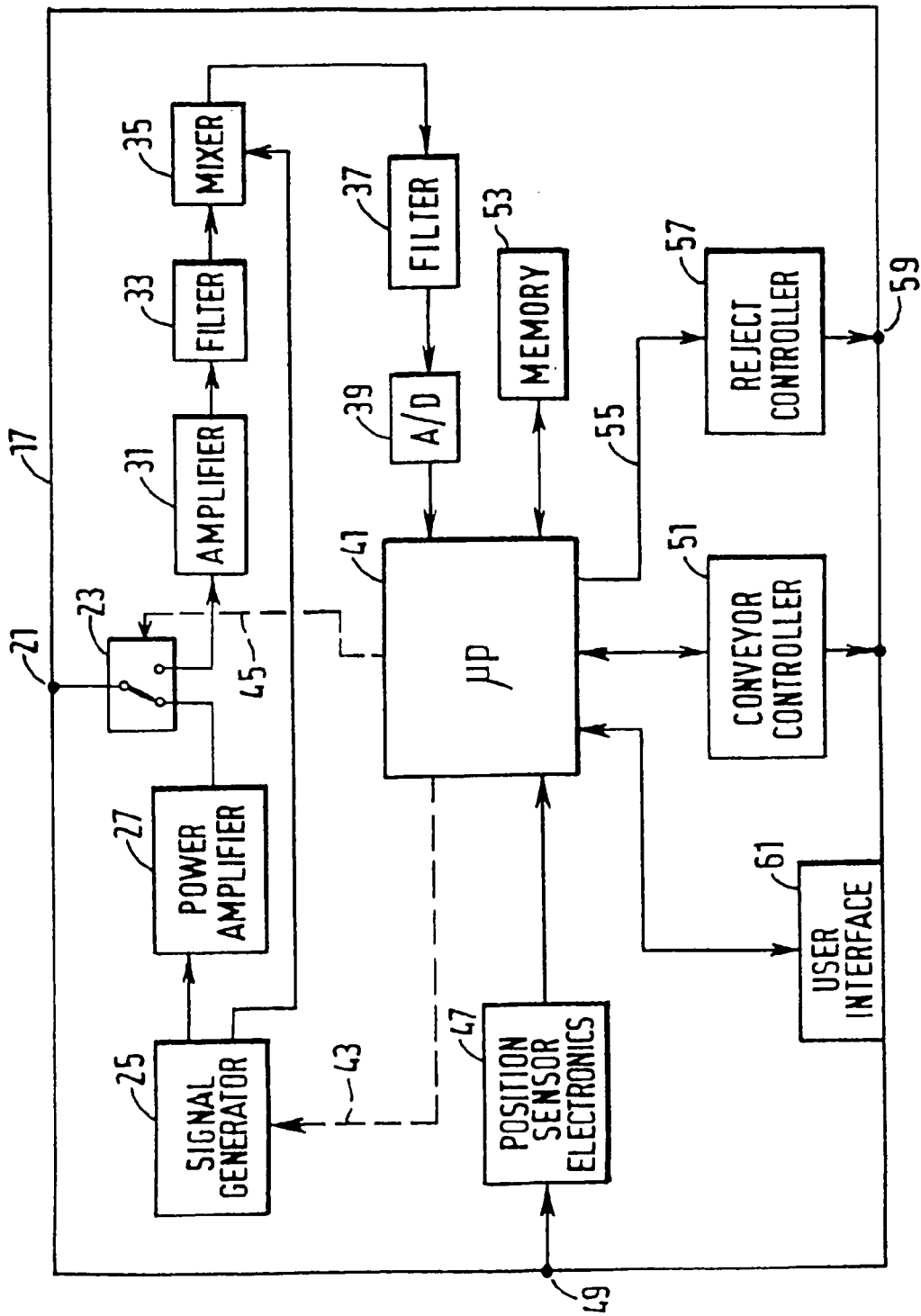
FIG. 1f is a block diagram of excitation and processing electronics that form part of and control the check weighing station shown in FIG. 1.

As shown in FIG. 1f, the computer control system 17 may also comprise a user interface 61 for allowing the user to program into the control system 17 what the correct mass of each sample should be for a given batch of product.

In certain embodiments, a single measurement of a sample's mass is determined for each vial. The accuracy of the measurement can be improved by taking an average of repeated measurements. However, the rate at which measurements can be made on the same sample is determined by the relaxation time discussed above. In particular, after the excitation signal has been removed, it takes approximately 5 times the relaxation time for the protons to return to their original aligned state in the static magnetic field, at which point a further burst of excitation current can be applied.

Separate measurements could be obtained either by using a number of different RF coils spatially separated along the Z-direction. Alternatively, the conveyor belt could be stopped each time a vial reaches the interrogation area and multiple measurements made.

Multiple measurements of the same sample may also be possible if the interrogation zone of the magnet and RF coil is large enough to allow multiple measurements to be taken considering the speed of the conveyor belt. In such an embodiment, the accuracy of the system will depend upon the homogeneity of the RF coil and the magnetic field within the interrogation zone as well as on the system signal to noise and the RF coil's fill factor. If the field patterns of the magnet and RF coil are known in advance, then this knowledge can be used to make corrections on the different measurement signals. Also, additional X, Y and Z coils (known in the art as shims) may also be provided to improve the homogeneity of the static magnetic field.

In one embodiment, a single vial is located within the RF coil 15 interrogation zone at any one time. FIG. 1a diagrammatically illustrates another embodiment in which the components of a check weighing station 3 allow multiple vials to be located within the RF coil 15 interrogation zone at the same time and which allow a mass measurement to be made of the sample within each vial individually. To achieve this, in such embodiment, in addition to the static magnet 13 and the RF coil 15, a separate pair of coils 71 and 73 are located either side of the conveyor belt 7, which operate to provide a magnetic field gradient across the conveyor belt 7. As a result of this gradient, the static magnetic field experienced by each of the glass vials will be different and thus the Larmor frequency of the sample in each of the three vials in the interrogation zone will be different. Consequently, each vial can be interrogated separately by applying three different narrow band RF pulses at the appropriate Larmor frequency.

Alternatively, a broad band RF pulse could be applied over the interrogation zone and the resulting MR signals from the samples can be resolved by taking the Fourier transform of the received signal after the excitation pulse has ended, as is standard practice in MR imaging.

With reference to FIG. 1a, the gradient coils are arranged to apply a gradient in the same direction as the static magnetic field which is generated by the magnet 13. As is well known in the art of magnetic resonance imaging, gradient coils can be arranged to provide magnetic field gradients in one or more of the X, Y or Z axes so that the entire volume of the interrogation zone can be spatially resolved. FIG. 1b illustrates an embodiment where the two gradient coils 71 and 73 are provided at opposite ends of the RF coil's interrogation zone. In this embodiment, the RF coil 15 comprises three separate portions 15a, 15b and 15c. As those skilled in the art will appreciate, by applying a magnetic field gradient along the length of the conveyor belt 7 through the interrogation zone, each of the samples can be interrogated separately or simultaneously in the same way as in the embodiment described with reference to FIG. 1a.

In the embodiments described with reference to FIGS. 1a and 1b, a plurality of samples were located within the interrogation zone and either interrogated separately or simultaneously. In these embodiments, since each of these samples will experience a slightly different magnetic field and will be in a different position relative to the RF coil, separate calibration data can be used for each of the sensing positions in order to try to reduce errors caused by inhomogeneities in the static magnetic field or in the RF coil.

In the above embodiments, the RF coil generated a magnetic field in the Z-direction along the direction of movement of the conveyor belt 7. The RF coil can be located at any angle relative to the DC magnetic field, provided the field which it generates is relatively homogenous over the sample being tested and provided it comprises a component which is orthogonal to the static magnetic field. FIG. 1c diagrammatically illustrates an embodiment where three separate RF coils 15d, 15e and 15f are provided under the conveyor belt 7, each of which is operable to generate an AC magnetic field in the Y-direction. This embodiment allows the samples in three vials to be tested simultaneously. It also allows the system to interrogate the sample in each vial three times, once by each of the RF coils.

In the above embodiments, a permanent magnet was used to generate the static magnetic field. As those skilled in the art will appreciate, electromagnets, current carrying coils or superconducting magnets could be used in place of the permanent magnet to generate the necessary DC magnetic field. Additionally, in the above embodiments, the DC magnetic field was applied across the conveyor belt in the X-direction. As those skilled in the art will appreciate, the DC magnetic field can be applied through the sample in any direction. For example, the north and south pole of the magnet may be placed above and below the conveyor with the RF coil being, for example, in the same orientation as in the first embodiment. FIG. 1d shows yet another embodiment in which a solenoid coil 75 is wound along a length of the conveyor belt 7 for generating the static magnetic field along the length of the conveyor belt 7, i.e. in the Z-direction. In this embodiment, the RF coil 15 is provided at one side of the conveyor 7 and a separate detector coil 77 is provided at the opposite side of the conveyor 7.

FIG. 1e shows a schematic plan view of a production line with an NMR check weighing station. Generally, the check weighing station 100 includes an in-feed section 101 comprising a conveyor belt or other transport mechanism, the check weighing section 102 containing the magnet, RF antenna and in part defining the interrogation zone 103, a reject section 104 leading to a reject buffer 105, and an out-feed section 106. The check weighing station may contain an operator panel 107.

There are other configurations which will allow a measurement of the mass of the sample to be obtained.

Continuously measuring the weight and humidity content of powders.

With NMR technology it is possible to acquire a signal that is linearly proportional to the number of hydrogen atoms in the measured sample. After calibration with known weights, this signal becomes a measure of the mass of that sample. This can be done continuously by carefully shaping the measurement probe to allow transport means to feed samples through the probe.

This procedure has been discussed above for liquids. The method is successful for liquid samples because the decay for solid matter is much faster than for liquids, and therefore this influence can be filtered out rather easily. Powders do decay faster than liquids, but again slower than the container material.

In order to be able to measure solids, it has to be taken into account that the FID decays much more rapidly than with fluids. In general, the behavior of the electronic resonant circuit of the excitation and measurement coil is such that the waiting times for detection of the response after the excitation pulse are dictated by the ring-down time of the probe (DEAD1) and the settling time of the digital detection bandwidth filters (DEAD2). Alternatively, a separate detection coil may minimize the waiting time after the excitation pulse.

After a sufficient amount of time, the contribution to the signal from the solid material and the powder dies out, leaving the signal of the liquid portion still available. It is then possible to determine the humidity of the powder by comparing the signal to calibration data that represents samples with known values for the property or characteristic being measured. To establish calibration, first the amount of time after the excitation pulse when the solid no longer contributes to the signal is determined. Then, known samples are presented to the system, measured at the above-mentioned time and then inserted in a calibration routine.

According to this method, the resolution of the measurement is increased. The technical elements of this improvement are related to increasing the basic field strength of the magnet and modifying the shape of the probe to enhance signal to noise ratio. Applying higher magnet fields can increase resolution and increase the signal/noise ratio.

Magnet: The main purpose of this element is to increase the field strength. This can be accomplished in several ways, for example, either by reducing the distance between the magnet poles or by applying more volume of the magnet material. In the latter case, the magnetic properties of the high permeability material may be limiting factors. In one embodiment this can be accomplished by increasing the strength of the magnet by about three times by limiting the bore and therefore the maximum allowable vial size. In general, the field strength is preferably maximized. For permanent magnets, a practical value that can be reached is in the range of about 0.1 T to about 1.3 T, in certain embodiments on the order of about 0.5 T.

Probe: It is preferred to make the probe (that also may apply the alternating magnetic field) as tightly fitting to the sample as possible. A limiting factor is determined by the necessary "play" or tolerance for the mechanical transport of the samples. The fill factor (ratio between the product volume and the effective volume of the excitation field) is one of the determining factors of the signal to noise ratio: S/N~sqrt (fill factor). Reducing the distance between the vials and the probe surfaces increases the fill factor, so for fill factor reasons, the distance should be minimized. Because of local B1 field inhomogeneities, some distance is needed. In certain embodiments, the samples are disposed within a distance of about 0.1 to about 10 mm from the surface of the probe. Larger distances could be applicable, but at the expense of worsening accuracy. The practical distance between the vials and the probe surfaces is largely determined by the tolerances of the vial diameters (generally on the order of about 0.5 mm). For maximum S/N, in one embodiment the vials are the determining factor, and thus the transport mechanism is not made to extend the vial diameter.

Pulse sequences: In addition to single 90° excitation pulses and the resulting FID's, other concepts are known in NMR-technology, such as the application of pulse sequences. One of them is the so-called OW4 sequence. In this sequence the first 90° pulse is followed by a series of 90° pulses, but with a 90° degree phase change. Each pulse of this series results in a so-called echo that effectively extends the FID to its origin, i.e. without waiting for DEAD1 and DEAD2. This way the signal/noise ratio is improved considerably. It is also possible to use two or more consecutive echoes and average the results in order to improve the accuracy.

Figure 2:
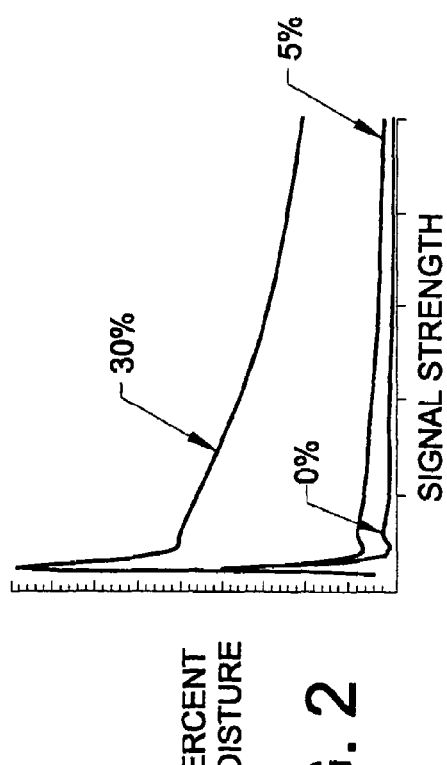
FIG. 2 is a graph that illustrates the different signal strengths related to various levels of humidity in powder samples.

The graph of FIG. 2 illustrates the different signal strengths related to various levels of humidity in powder samples. As shown in FIG. 2, by comparing the amplitudes of known moisture percentages, it is possible to establish a relationship to determine moisture content out of the NMR signals. The signals may be acquired with the same type of measurement as the weight determining case and therefore can be combined into a single measurement run.

With the concept of investigating "dead times" it is possible to discriminate between physical properties of materials. By use of NMR techniques, it is therefore possible that physical phase transitions and viscosity variation can be measured. Also, by use of these techniques, homogeneity of colloids and suspensions can be evaluated.

For example, to determine physical properties of materials, first take a 'dead time' of 10 microseconds. In this manner, the FID is measured in an early stage and therefore there is a lot of solid content. Setting subsequently the 'dead time' to 300 microseconds, the solid portion is died out and only the liquid component is measured. This yields information on concentration. There also known to those of skill in the art, special pulse sequences to determine this in one experiment.

To determine viscosity and phase transitions, the viscosity is very much related to T1, a magnetisation characteristic. When presenting samples relatively quickly after they have entered the main magnetic field, they are not fully magnetised and therefore small differences in T1 will result in large amplitude differences in the FID-amplitude.

To determine homogeneity of suspensions, the shape of the FID will change when an originally homogeneous suspension is becoming inhomogeneous. The quantitative data is calibrated against known samples. Therefore using a standardized, known sample, the ideal FID is first determined. Then, using spectroscopic (statistical) data analysis techniques, the deviations can be determined and quantified.

EXAMPLES

In an example testing repeatability, single-pulse measurements were applied to the samples. A range of 7% was observed. When applied to the contents being 1 g, this means a sigma of 70/6 or 12 mg (assuming the range being 6 sigma). Testing calibration and reproducibility, each sample vial was measured and the result entered into a calibration table with the known value, resulting in a calibration curve and yielding a standard deviation value. The results showed that the standard deviation of the reproducibility testing was 14 mg, being very close to the repeatability result. Optimization of the quality of the measurements can therefore be focused on increasing the signal/noise ratio.

The applicability of NMR techniques for non-contact check weighing of powder material was demonstrated for pomoic acid used as placebo.

Method

To assess the properties of this material related to NMR, the following experiments were conducted:
1. determine T1 in order to achieve insight of magnetizing aspects;
2. determine static signal variation to assess S/N;
3. determine static signal with reposition effects;
4. determine calibration with known weights.

The measurement conditions were:

23 MHz magnet;

DEAD1=4 microseconds;

DEAD2=3 microseconds;

Filter setting=1 MHz;

Number of sample points for FID=1024.

T1 Measurement

Figure 3:
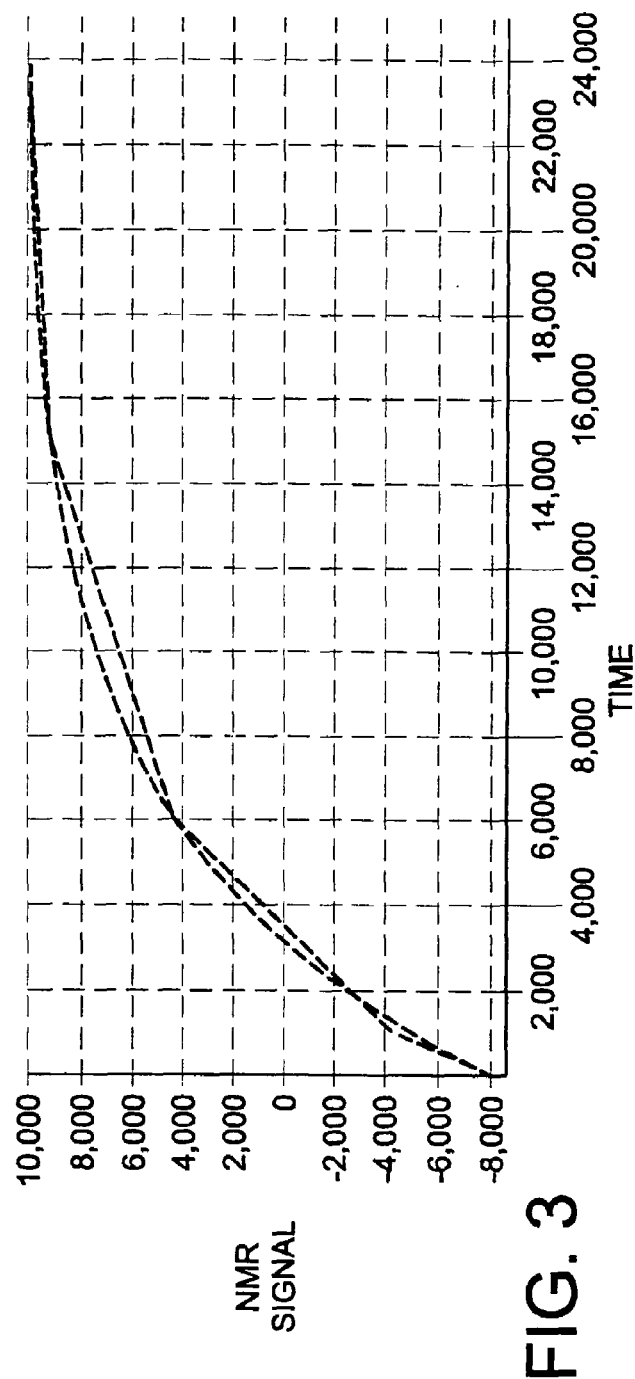
FIG. 3 is a graph showing the time (T1) needed to magnetically align the spins.

Using the well-known inversion recovery sequence, the specific time needed to magnetically align the spins can be determined. This is an indication of how measurement speed can affect the signal to noise ratio and hence the accuracy. The T1 is defined by the time needed to reach 63% of the saturated value. It is determined by fitting the measurement curve with an exponential function as shown in the graph of FIG. 3. The statistics used to determine the time constant that goes with the graph of FIG. 3 are presented in the screenshot chart of FIG. 4.

Figure 4:
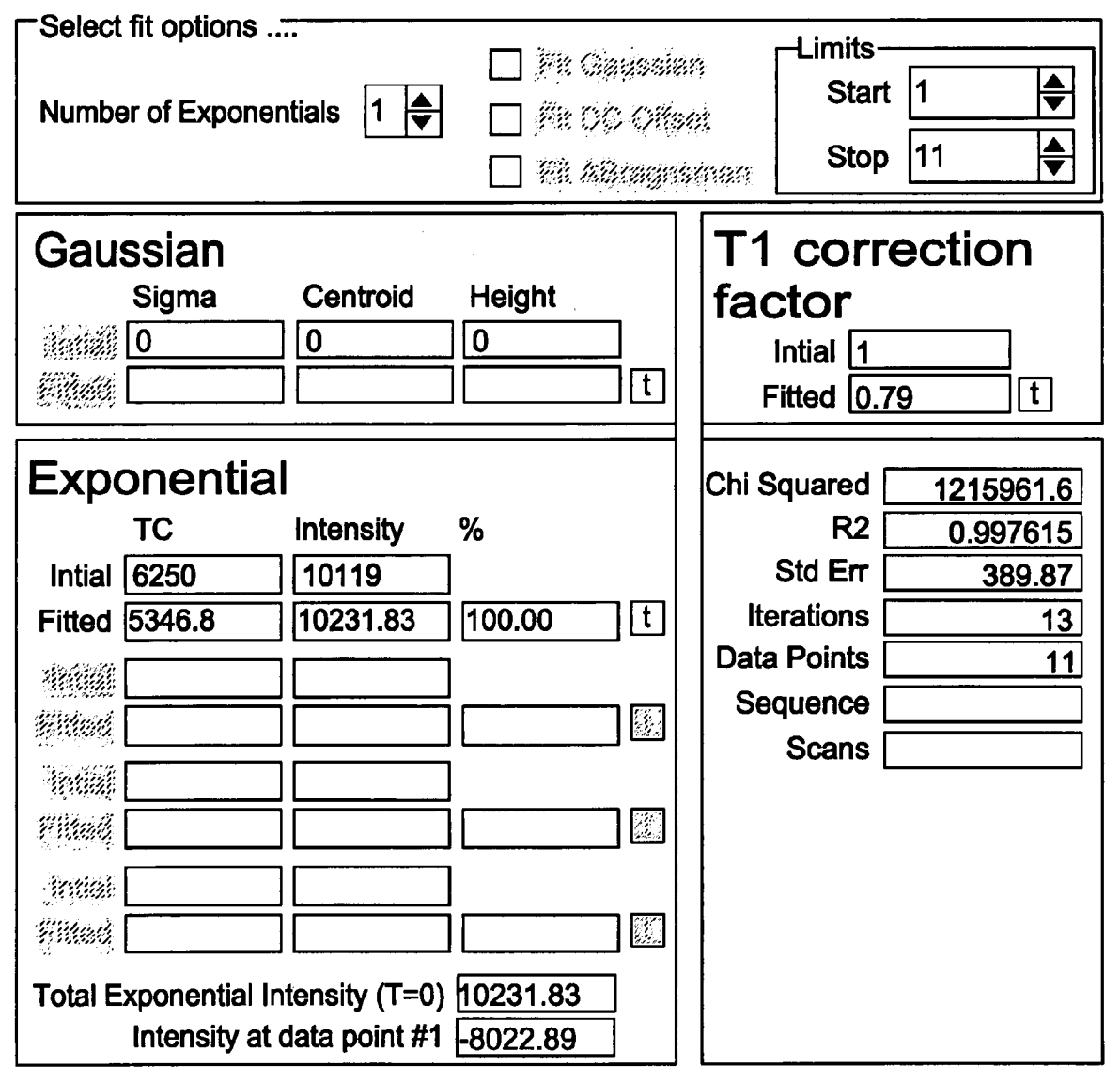

The data of FIG. 4 show that the T1 is of the order of 5 s, which is comparable with water solutions that have been investigated. This also means that at vial speeds greater than 50 vials per minute, the material will not be completely magnetized and therefore S/N is an important issue. However, although the signal strength for solids is not high, temperature effects are likely to have a lesser effect than with liquid fluids. Transport will be easier since sloshing effects are no issue.

Static measurement to determine basic Signal to Noise Ratio (S/N)

Two tubes with the sample material have been employed to do repeat FID measurements while leaving the samples in place. The results are shown in Table 1 below:

TABLE 1

|  | sample 3 | sample 9 |
|---|---|---|
| average | 141.668 | 136.312 |
| Stdev | 5.439648 | 5.023886 |
| Relative | 0.038397 | 0.036856 |

Static measurement with samples taking in and out

This experiment determines the effect of not completely magnetized samples before the measurement. The results are shown in Table 2 below:

TABLE 2

|  | sample3_repeat | sample9_repeat |
|---|---|---|
| average | 100.328 | 103.7167 |
| Stdev | 5.620907 | 5.209913 |
| Relative | 0.056025 | 0.050232 |

This result shows that taking samples in and out leads to increase in measurement error (sigma) from 3.7% to 5.3%. Since there was extremely little play for the samples being positioned it is more likely another indication that S/N plays a major role.

Calibration

The test was conducted twice. The first time tubes with small diameters were used because the magnet available had a small bore. This meant that for this case only, samples less than 250 mg could be used.

Figure 5:
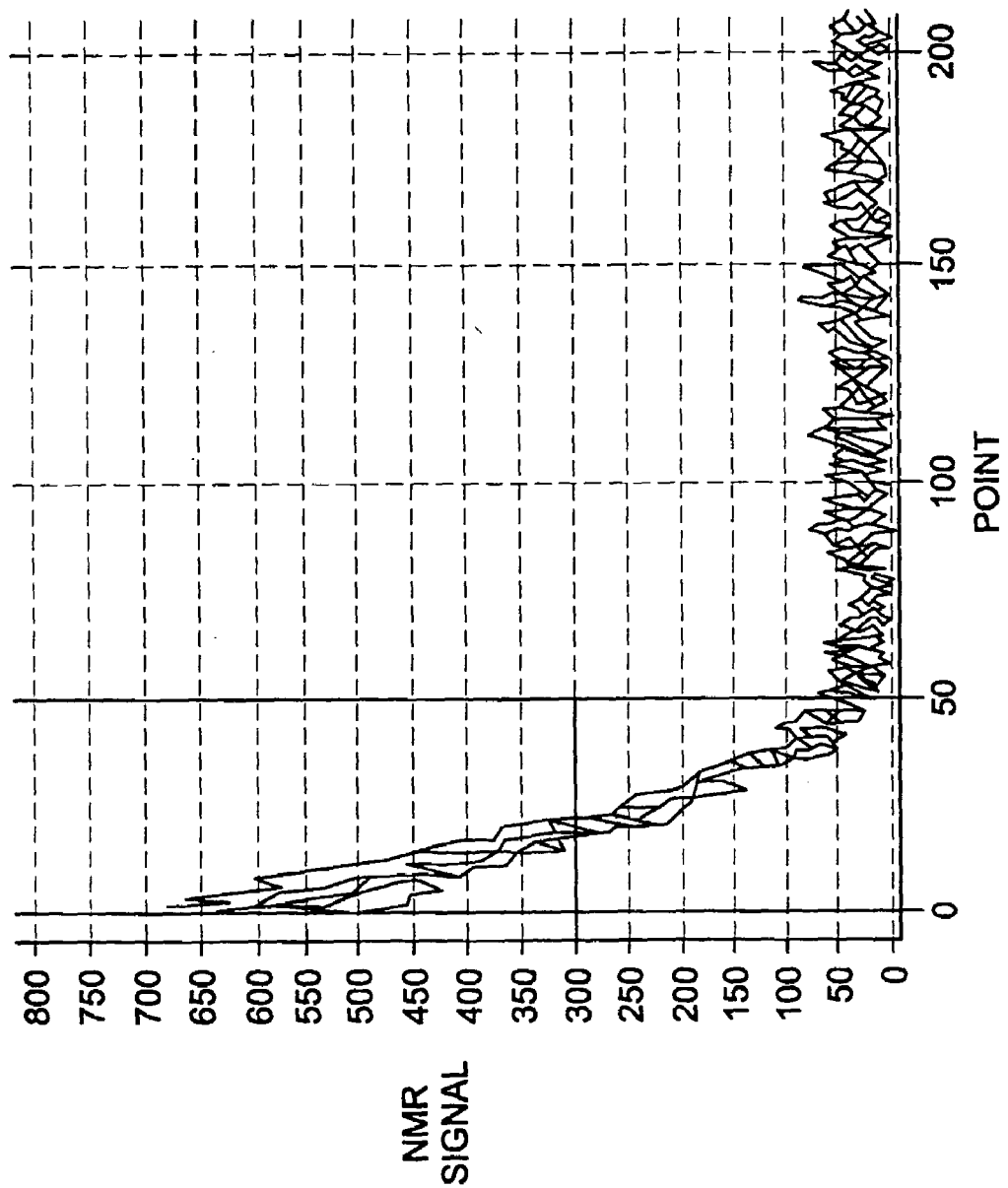
FIG. 5 is a graph of NMR signal values for free induction decay (FID).
Figure 6:
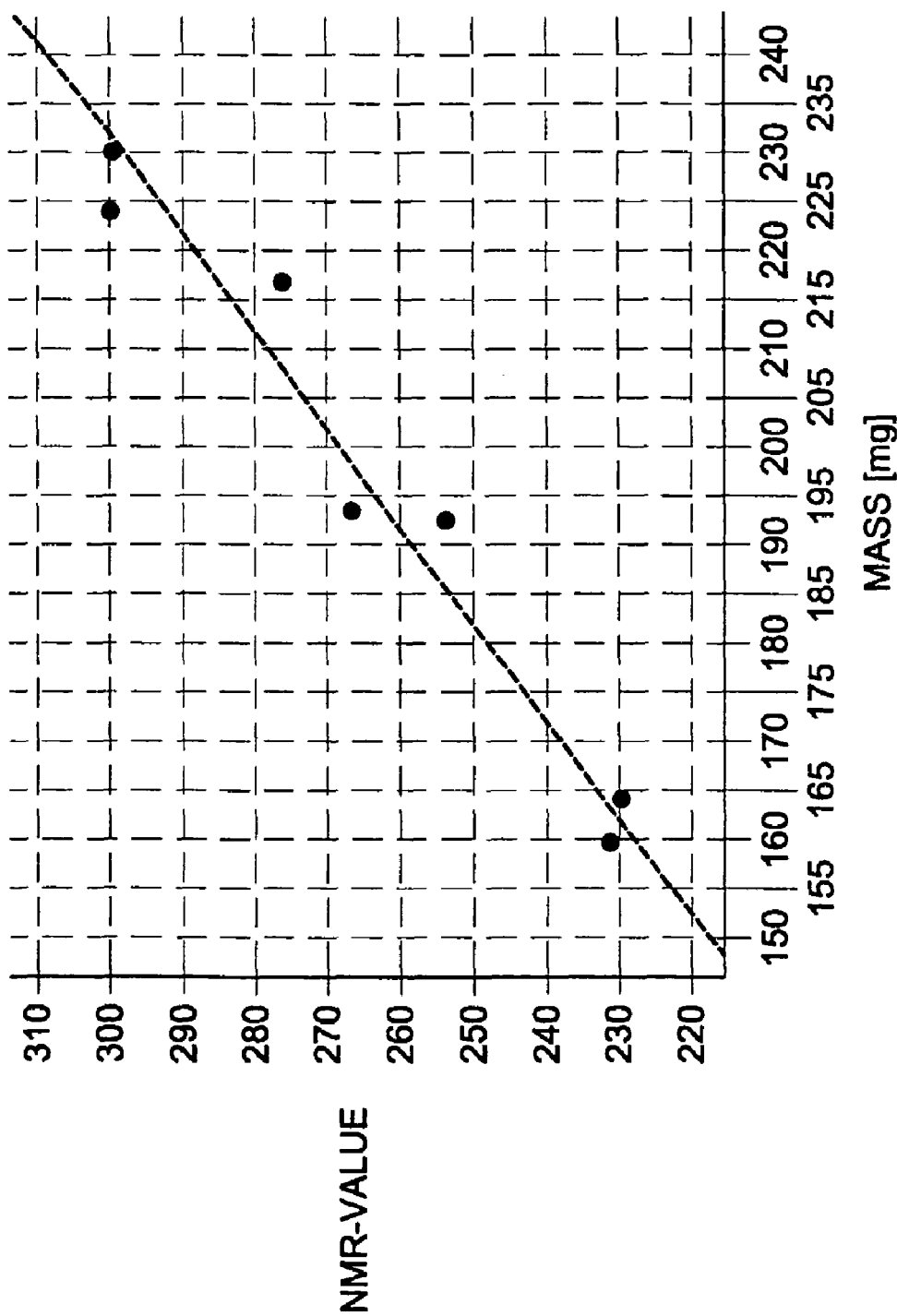
FIG. 6 is a calibration curve showing the fit between known weights and the NMR signal values.

The calibration curve of FIG. 6 shows the fit between known weights and NMR signal values shown in the graph of FIG. 5. The statistics for this data are presented in Table 3 below.

TABLE 3

| Number of Points | 7 |
|---|---|
| Slope | 1.02 |
| Value intercept | 64.52 |
| Conc. Intercept | −63.3569 |
| Correlation Coefficient | 0.9775 |
| Standard deviation | 5.5044 |
| Variance | 30.2985 |

Figure 7:
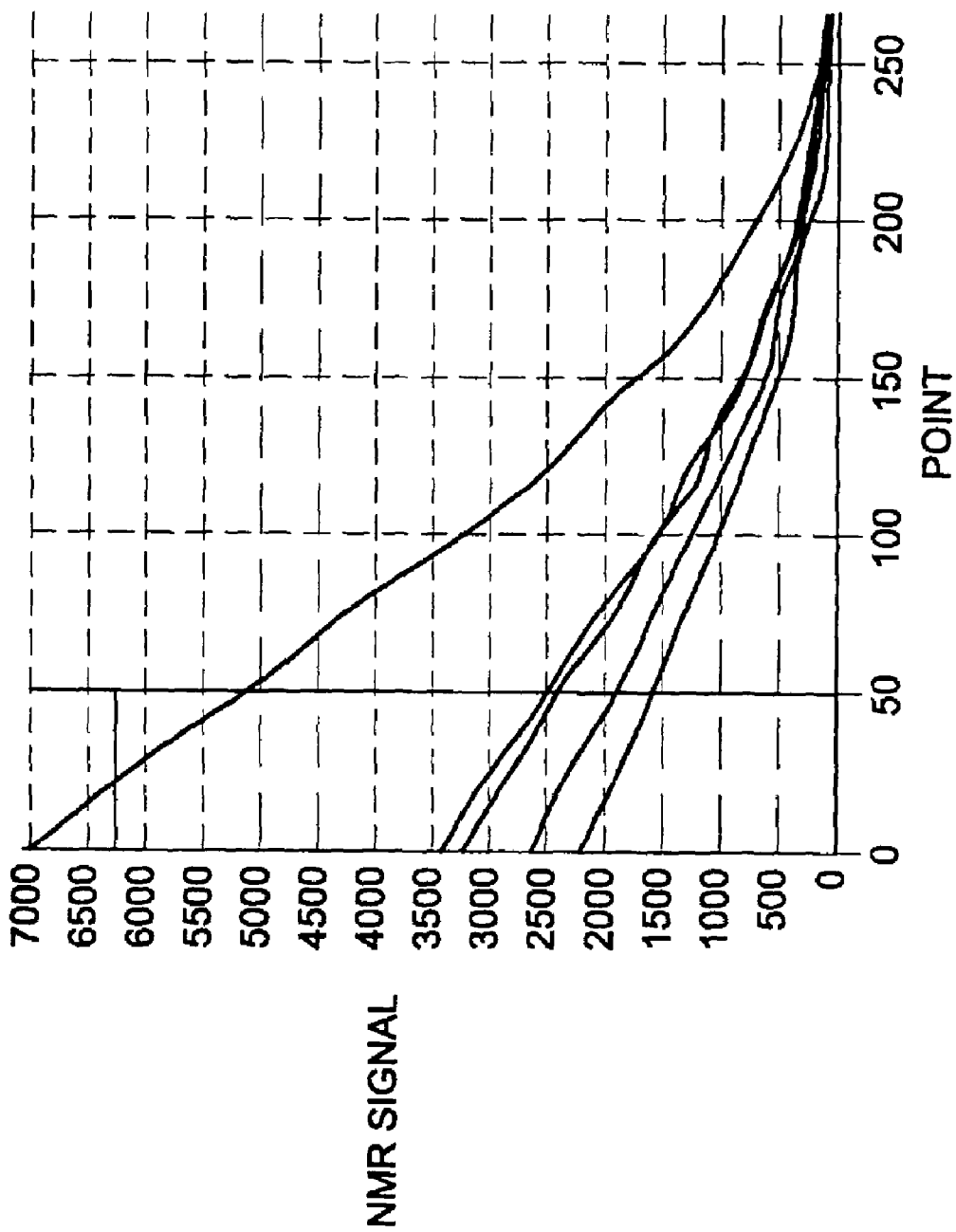
FIG. 7 is a graph of NMR signal values for free induction decay (FID).
Figure 8:
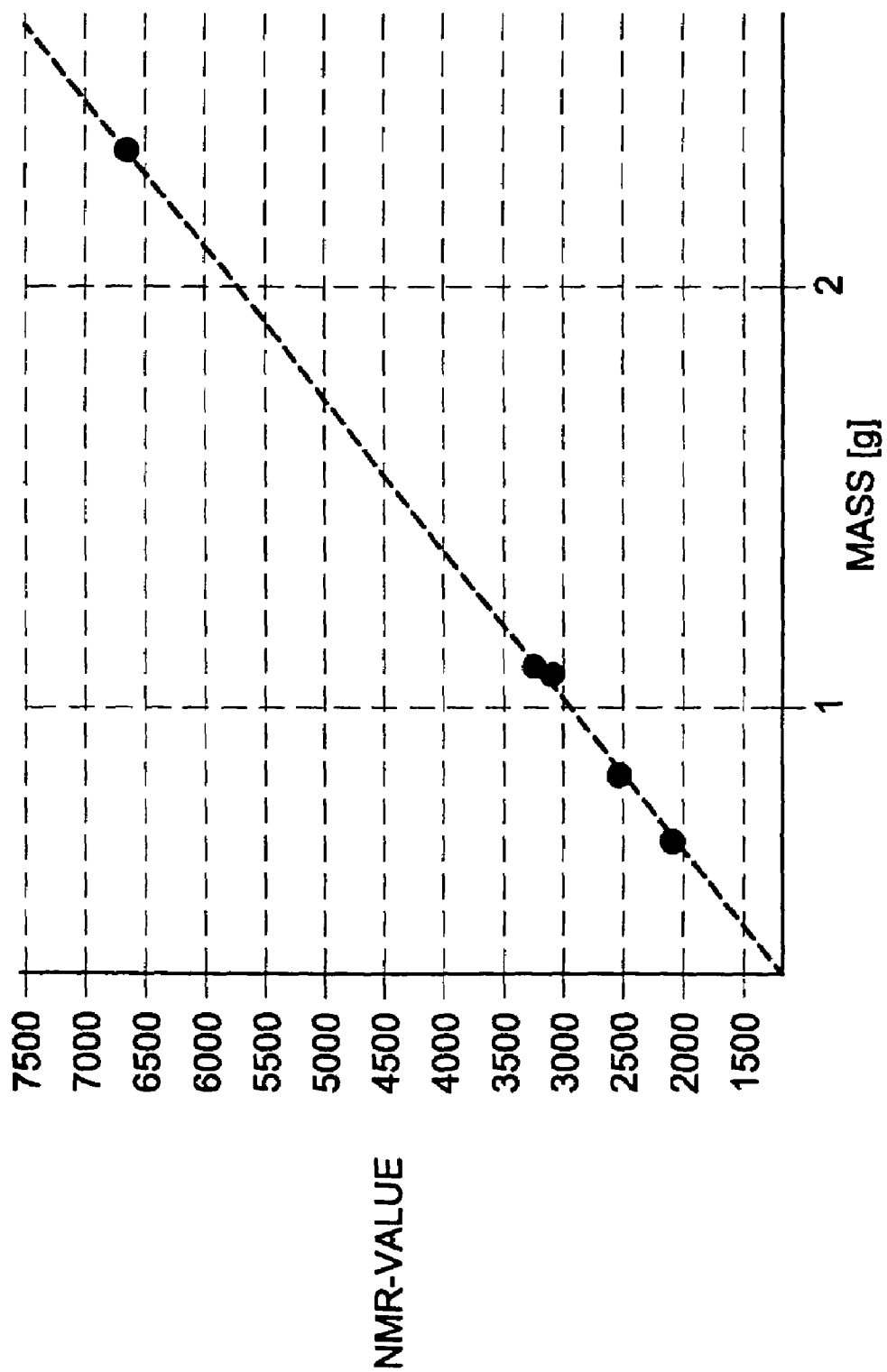
FIG. 8 is a calibration curve showing the fit between known weights and the NMR signal values.

Using a magnet with a larger bore allowed taking samples of the order of 1–2 g. The FID's that comprise the calibration are presented in FIGS. 7 and 8, showing the results of the wider tubes. The calibration data are shown in Table 4.

TABLE 4

| Number of Points | 5 |
|---|---|
| Slope | 2619.47 |
| Value intercept | 157.55 |
| Conc. Intercept | −0.06 |
| Correlation Coefficient | 1.00 |
| Standard deviation | 0.02 |
| Variance | 0.00 |

Along the course of preparing the samples it appeared to be difficult to fill the tubes in a controlled way. The powder showed some sticky behavior and therefore some of the inaccuracies can be explained.

According to these methods, it is possible to determine the weight of the powder, although the accuracy is less than realized with fluid under similar circumstances. However, the effects of the vial stoppers can be filtered out, such as by RF-field. Filtering out stoppers can be accomplished by taking into account that most stoppers have shorter T2 (spin-spin relaxation times) than the powders under consideration.

As an example of one of the calibration techniques to determine the properties of the specific stoppers, start with short 'dead times' to determine the signal of the solid component. Then, stepwise increase the 'dead time' until the solid signal is vanished in the noise. It is no problem to take a large safety margin since the liquid component signal takes orders of magnitude longer to die out.

In other instances, the RF field may be designed such that the extent of the field is limited to the height that is covered by the product. In this way, there will be no NMR signal coming from the stopper region. Any powder sticking to the stopper will not contribute to the signal either.

In one example, sample vials contained powder that had the tendency to stick to the sides of the vials. Moreover, due to transportation a clearly visible amount of powder adhered to the rubber stopper. With tapping, most of the powder was forced to the bottom. This was not possible with the product on the stoppers (which during measurement can be shielded by an aluminum cap). To assess the influence of stopper material and product adhering to it, a measurement was repeated with and without the stopper. The results of the example illustrated that the amplitude of the signal without the stoppers was 0.16% higher than with stoppers. While potentially due to other effects such as temperature, the example showed that the influence of stoppers was not likely to be significant in certain embodiments.

Incomplete Magnetisation

In the application of NMR techniques to determine characteristics of the contents of containers, such as vials, in a non-stationary manner, prior to the sample being in the measurement position the sample is moving through the magnetic field and is therefore being pre-magnetised (or pre-polarised). At the measurement position, the sample may be excited with an excitation pulse, for example a 90° pulse. This pulse causes the spins of the protons to precess in a plane, perpendicular to the main magnetic field. The relaxation process is dominated by dephasing of the spin precessions of the individual protons, and this free induction decay (FID) signal is measured. The amplitude of this signal is linearly proportional to the amount of protons in the sample, and therefore a sample calibration allows the method to be used as a measurement method, such as for weighing.

The process of polarization is a process with a typical time-constant, the T1 (spin-lattice constant). Generally NMR measurements can be taken when the pre-magnetization is complete. This stage is reached when taking approximately 5 times T1 as a magnetization period. For many pharmaceutical products, the T1 is of the order of 1 second. For completely magnetised NMR measurements, a pre-magnetization step of 5 seconds would be necessary.

Figure 9:
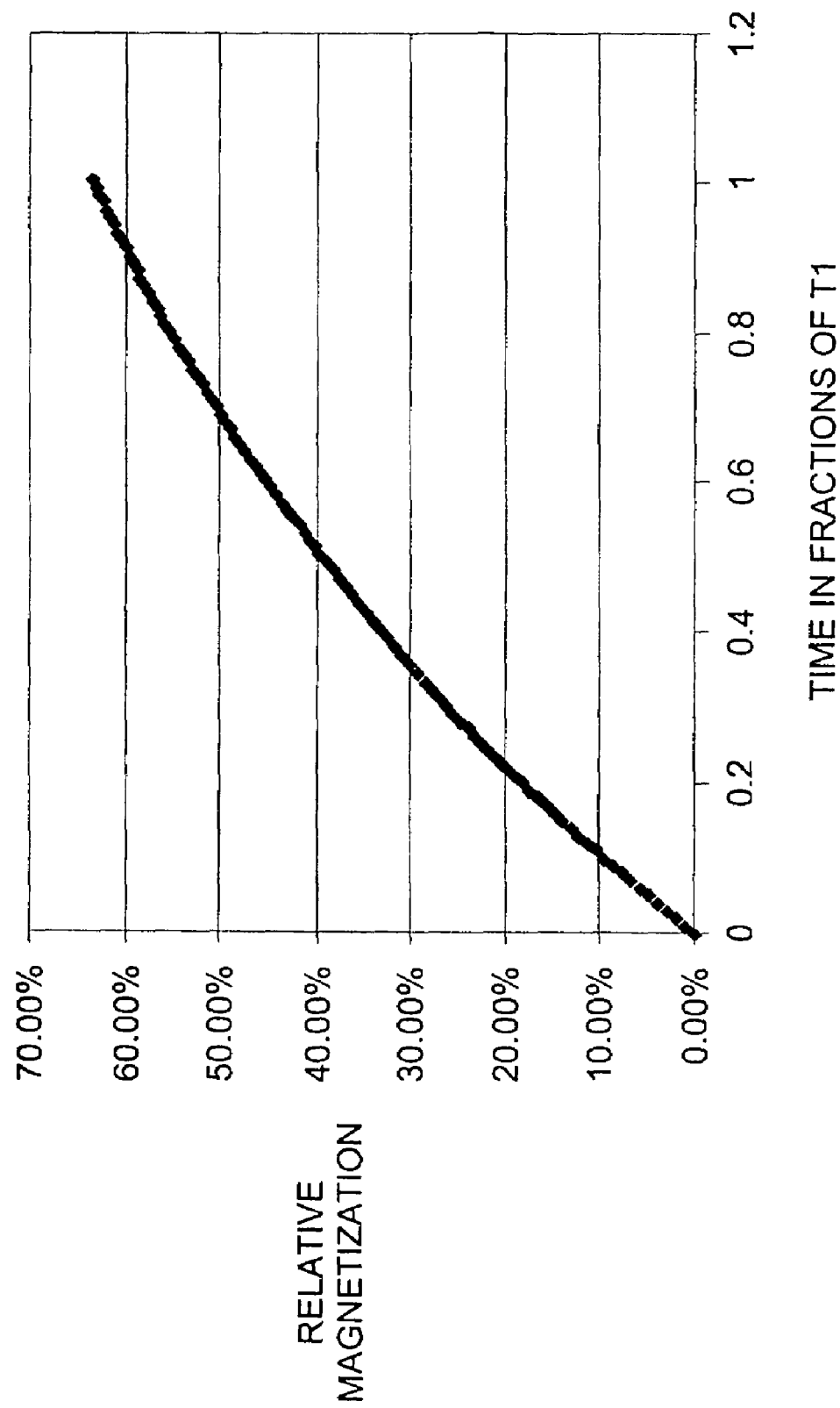
FIG. 9 is a graph showing a polarisation curve comparing relative magnetization to time in fractions of T1.

In embodiments in which the method is applied to fast moving samples, the measurement is applied to incompletely magnetised samples and this measurement is accurate enough if the history (in terms of exposure to the magnetisation field) of every subsequent sample is identical, for example: the T1 influencing factors are known (via specific calibration) and can be incorporated into the measurement calculations (for example, temperature), and the speed of every subsequent sample does not vary, or is accurately known and can be compensated for. The graph of FIG. 9 shows a magnetisation curve and the consequence of having typically only half of a T1 available for magnetisation, yielding only 39% of magnetisation.

Although the invention has been described in detail through the above detailed description and the preceding examples, these examples are for the purpose of illustration only and it is understood that variations and modifications can be made by one skilled in the art without departing from the spirit and the scope of the invention. It should be understood that the embodiments described above are not only in the alternative, but can be combined.

The invention claimed is:

1. An improvement in a magnetic resonance method for determining the mass of samples in a production line wherein the samples comprise powdered solid materials, comprising:

applying a first magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone;

monitoring energy emitted by the sample as the net magnetisation of the sample returns to its original state and generating an output signal having a characteristic which is proportional to the energy emitted;

comparing the output signal characteristic with like data obtained from at least one similar sample of known mass; and, determining the mass of the sample; characterised by:

applying the first magnetic field having a field strength in the range of about 0.1 T to about 1.3 T;

applying the alternating magnetic field to the sample;

monitoring the free induction decay energy of the sample and generating an output free induction decay signal corresponding thereto.

2. An improvement in a magnetic resonance method for determining the mass of samples in a production line wherein the samples comprise powdered solid materials, comprising:

applying a first magnetic field in a first direction in an interrogation zone for creating a net magnetisation within a sample located within the interrogation zone;

applying an alternating magnetic field with a probe in a second direction in the interrogation zone for temporarily changing the net magnetisation of the sample located within the interrogation zone;

monitoring energy emitted by the sample as the net magnetisation of the sample returns to its original state and generating an output signal having a characteristic which is proportional to the energy emitted;

comparing the output signal characteristic with like data obtained from at least one similar sample of known mass; and, determining the mass of the sample;

characterised by:

disposing the samples within a distance of about 0.1 to about 10 mm from the surface of the probe;

applying the alternating magnetic field to the sample; and monitoring the free induction decay energy of the sample and generating an output free induction decay signal corresponding thereto.

3. The method of claim 2 wherein applying the alternating magnetic field in the second direction comprises applying a series of pulses of alternating magnetic field to the sample.

4. The method of claim 1, 2 or 3 including continuously feeding samples through the interrogation zone and generating an output signal proportional to the weight of the samples.

5. The method of claim 1, 2 or 3 including determining the humidity content of each sample by determining for the samples the time at which the contribution to the signal from the solid materials dies out; and comparing the remaining contribution to the signal still available from any liquid portion to like data that represents samples with known values for humidity.

6. The method of claim 1, 2 or 3 wherein the sample is carried in a container having a stopper, including filtering out the signal correlating to the stopper based on calibration data.

7. The method of claim 1, 2 or 3 wherein the sample is carried in a container having a stopper, including eliminating any signal correlating to the stopper by applying the alternating magnetic field selectively to the portion of the container holding the sample.

8. The method of claim 1 or 2 wherein homogeneity of the samples comprising suspensions is monitored by detecting free induction decay shape deviations from like calibration data based on known homogeneous suspension samples.

9. The method of claim 1 or 2 wherein viscosity and phase transitions are determined by applying the alternating magnetic field to the samples after entering the first magnetic field, and detecting large differences in the free induction decay amplitude from like calibration data.

10. The method of claim 1 or 2 wherein viscosity and phase transitions are determined by applying the alternating magnetic field to the samples after entering the first magnetic field, but before the samples are fully magnetized, and detecting large differences in the free induction decay amplitude from like calibration data.

11. The method of claim 1 or 2 wherein the energy emitted by the samples is monitored and the output signal is generated prior to the samples reaching complete magnetization.

12. The method of claim 1 or 2 wherein the output signal characteristic is output signal amplitude.

13. An improvement in a magnetic resonance method for determining the mass of samples in a production line wherein the samples comprise powdered solid materials, comprising:

applying a first magnetic field in a first direction in an interrogation zone for creating a net magnetisation within a sample located within the interrogation zone;

applying an alternating magnetic field in a second direction in the interrogation zone for temporarily changing the net magnetisation of the sample located within the interrogation zone;

monitoring energy emitted by the sample as the net magnetisation of the sample returns to its original state and generating an output signal having a characteristic which is proportional to the energy emitted;

comparing the output signal characteristic with like data obtained from at least one similar sample of known mass; and, determining the mass of the sample;

characterised by:

applying the first magnetic field having a field strength greater than or equal to 0.5 T;

applying the alternating magnetic field to the sample;

monitoring the free induction decay energy of the sample and generating an output free induction decay signal corresponding thereto.

* * * * *